(12) United States Patent
Hu et al.

(10) Patent No.: US 8,722,030 B2
(45) Date of Patent: May 13, 2014

(54) COMPOSITE VACCINE ADJUVANT

(75) Inventors: Yunzhang Hu, Kunming (CN); Ningzhu Hu, Kunming (CN); Haixuan Wang, Kunming (CN)

(73) Assignee: Institute of Medical Biology, Chinese Academy of Medical Sciences and Peking Union Medical College, Yunnan (CN)

( * ) Notice: Subject to any disclaimer, the term of this patent is extended or adjusted under 35 U.S.C. 154(b) by 0 days.

(21) Appl. No.: 13/805,315

(22) PCT Filed: Mar. 22, 2011

(86) PCT No.: PCT/CN2011/072034
§ 371 (c)(1),
(2), (4) Date: Apr. 29, 2013

(87) PCT Pub. No.: WO2012/100453
PCT Pub. Date: Aug. 2, 2012

(65) Prior Publication Data
US 2013/0202651 A1 Aug. 8, 2013

(30) Foreign Application Priority Data

Jan. 26, 2011 (CN) .......................... 2011 1 0027724

(51) Int. Cl.
*A61K 47/14* (2006.01)
(52) U.S. Cl.
USPC ..................................... 424/70.13; 424/278.1
(58) Field of Classification Search
None
See application file for complete search history.

(56) References Cited

U.S. PATENT DOCUMENTS 8,431,517 B2 * 4/2013 Song .............................. 510/220

FOREIGN PATENT DOCUMENTS

| CN | 101219129 A | 7/2008 |
| CN | 101444623 A | 6/2009 |
| CN | 101791302 A | 8/2010 |

OTHER PUBLICATIONS

International Search Report of international application No. PCT/CN2011/072034, dated Nov. 3, 2011.

* cited by examiner

*Primary Examiner* — Robert A Wax
*Assistant Examiner* — Danah Al-Awadi
(74) *Attorney, Agent, or Firm* — J.C. Patents

(57) ABSTRACT

The invention provides a composite vaccine adjuvant, which is comprised of sodium ferulate and zinc hydroxide in a mass ratio of 10:1~50:1. When the composite vaccine adjuvant and vaccine used in combination, the humoral immunity response is enhanced effectively, the enhanced effects is similar with aluminum adjuvant, superior to single sodium ferulate adjuvant and single zinc hydroxide adjuvant. It is not only atoxic, safety, but also reliable in the range of immune dose. The composite vaccine adjuvant with easily obtained and commercially available raw materials, is low cost, stable performance and simple preparation technology, which can be used as an adjuvant of hepatitis B vaccine, gene-engineered vaccine, virus vaccine and so on.

10 Claims, 4 Drawing Sheets

Fig. 2: the mice serum antibody levels of anti-HBs IgG in each experimental group within 28 weeks (1:N)( low-dose group of sodium ferulate)

Fig. 3: the mice serum antibody levels of anti-HBs IgG in each experimental group within 28 weeks (1:N)(medium dose group of sodium ferulate).

Fig. 4: the mice serum antibody levels of anti-HBs IgG in each experimental group within 28 weeks (1:N)( high dose group of sodium ferulate)

COMPOSITE VACCINE ADJUVANT

TECHNICAL FIELD

This present invention relates to a composite vaccine adjuvant, which belongs to the technical field of immunology.

BACKGROUND ART

Sodium ferulate, with a chemical name: 3-methoxy-4-sodium hydroxycinnamate, molecular formula: $C_{10}H_9NaO_4$, molecular weight: 216.7, structural formula shown in FIG. 1, exhibits generally in the form of dihydrate. The molecular formula of the dihydrate is $C_{10}H_9NaO_4.2H_2O$, and the molecular weight is 252.20. Sodium ferulate has many pharmacological effects, such as relaxing blood vessels, antiplatelet activity, antioxidantion, free radical scavenging and so on.

Zn is an essential trace element for all organisms. In human subjects, the body's growth and development cannot be separated from zinc. The nervous, reproductive and immune systems are influenced by the Zn levels in vivo. The relationship between Zn and the immune system is particularly complex, and it is mainly reflected in the following four aspects. ① The daily intake and assimilation of Zn depends on components of diet, individual age and health. ② Zn has an indirectly effect on immune system because it is a cofactor in more than 300 kinds of enzymes with biological activity. ③ Zn has a direct effect on the production, maturation and function of lymphocytes. ④ Zn can influence the function of immunostimulants. By utilizing the above characteristics of Zn, zinc preparation adjunctive therapy is used in the treatment of some diseases, i.e. a certain dose of zinc preparations is given to patients while conventional therapy, thereby achieving a good curative effect. The beneficial therapeutic effects of Zn on many clinical experiments, such as infectious diseases, autoimmune diseases and vaccination and so on, have already been confirmed now.

The hotspot of the present vaccine research and development is vaccine adjuvant, and an ideal vaccine adjuvant has advantages of safety, validity, targeting and economy. The present aluminum adjuvant with the longest history and most widely usage has been authorized for human body, which improve significantly the body's immune response relying on the repository effects and immune-stimulating effects. However, its defects as a vaccine adjuvant in safety and targeting are still unsolved. Other potential candidates being studied or been confirmed as this kind of adjuvant have not been approved for human use for their problems in validity, safety, and economy.

Zinc hydroxide, with chemical formula: $Zn(OH)_2$, and formula weight: 99.4046, is similar with aluminum adjuvant in isoelectric point and water-solubility, easy to be prepared and low in costs.

DISCLOSURE OF THE INVENTION

To solve the problems of the existing vaccine adjuvant, such as suctoxic side effects and high in price and so on, the present invention provides a novel composite vaccine adjuvant upon a lot of experiments and creative work, which is safe, valid, steady and cheap.

The present invention provides a composite vaccine adjuvant, characterized in that said vaccine adjuvant is comprised of sodium ferulate and zinc hydroxide in a mass ratio of 10:1~50:1.

Sodium ferulate, with chemical name: 3-methoxy-4-hydroxycinnamate, molecular formula: $C_{10}H_9NaO_4$, molecular weight: 216.7, structural formula shown in FIG. 1, exhibits generally in the form of dehydrate. The molecular formula of the dehydrate is $C_{10}H_9NaO_4.2H_2O$, and the molecular weight is 252.20.

Chemical formula of said zinc hydroxide is $Zn(OH)_2$, and the formula weight is 99.4046.

Recommended dosage of said sodium ferulate in the body as a vaccine adjuvant is 10-50 mg.

Recommended dose of zinc hydroxide in the body as a vaccine adjuvant is 0.25-1.5 mg.

The immune response induced by said composite vaccine adjuvant is humoral immunity.

Said sodium ferulate is a commercial medical product.

Said zinc hydroxide is a commercial medical product.

Comparing with the prior art, the present invention has the following advantages and effects: (1) The composite vaccine adjuvant comprised of sodium ferulate and zinc hydroxide is non-toxic, non-cumulative toxicity, safe and reliable in the range of immunizing dosage. (2) The composite vaccine adjuvant comprised of sodium ferulate and zinc hydroxide can induce antigen-specific humoral immune response effectively, which has a better effect than a single aluminum adjuvant on inducing humoral immune response, a single sodium ferulate adjuvant and a single zinc hydroxide adjuvant. (3) The composite vaccine adjuvant with easily obtained and commercially available raw materials, is low cost, stable performance and simple preparation technology, which can be used as an adjuvant of hepatitis B vaccine, gene-engineered vaccine, virus vaccine and so on.

DESCRIPTION OF EMBODIMENT

Figure 1:
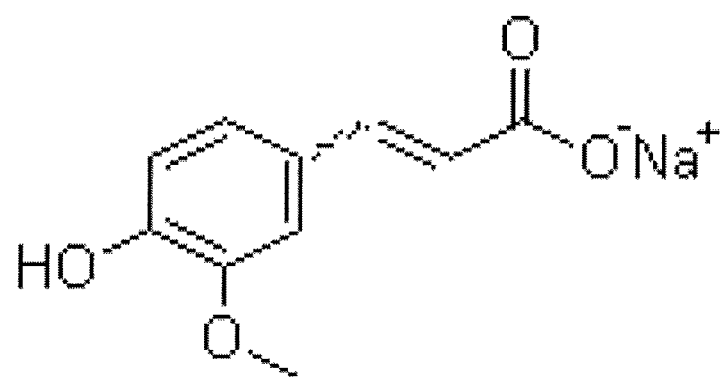
FIG. 1 shows the molecular structural formula of sodium ferulate.

The present invention is further described in connection with the following embodiments.

Embodiment 1

Took the commercial medical sodium ferulate 10 mg and zinc hydroxide 1 mg, mixing thoroughly to obtain the composite vaccine adjuvant.

The sodium ferulate in the embodiment 1 was purchased from Fujian Mindong Lijiexun Pharmaceutical Co., Ltd. The zinc hydroxide was provided by the Tianjin Guangfu Fine Chemical Research Institute.

Embodiment 2

Took the commercial medical sodium ferulate 25 mg and zinc hydroxide 1 mg, mixing thoroughly to obtain the composite vaccine adjuvant.

The source and quality of each component in this embodiment were the same as those in the embodiment 1.

Embodiment 3

Took the commercial medical sodium ferulate 50 mg and zinc hydroxide 1 mg, mixing thoroughly to obtain the composite vaccine adjuvant.

The source and quality of each component in this embodiment were the same as those in the embodiment 1.

Embodiment 4

Took the commercial medical sodium ferulate 15 mg and zinc hydroxide 1 mg, mixing thoroughly to obtain the composite vaccine adjuvant.

The source and quality of each component in this embodiment were the same as those in the embodiment 1.

Embodiment 5

Took the commercial medical sodium ferulate 20 mg and zinc hydroxide 1 mg, mixing thoroughly to obtain the composite vaccine adjuvant.

The source and quality of each component in this embodiment were the same as those in the embodiment 1.

Embodiment 6

Took the commercial medical sodium ferulate 30 mg and zinc hydroxide 1 mg, mixing thoroughly to obtain the composite vaccine adjuvant.

The source and quality of each component in this embodiment were the same as those in the embodiment 1.

Embodiment 7

Took the commercial medical sodium ferulate 35 mg and zinc hydroxide 1 mg, mixing thoroughly to obtain the composite vaccine adjuvant.

The source and quality of each component in this embodiment were the same as those in the embodiment 1.

Embodiment 8

Took the commercial medical sodium ferulate 40 mg and zinc hydroxide 1 mg, mixing thoroughly to obtain the composite vaccine adjuvant.

The source and quality of each component in this embodiment were the same as those in the embodiment 1.

Embodiment 9

Took the commercial medical sodium ferulate 45 mg and zinc hydroxide 1 mg, mixing thoroughly to obtain the composite vaccine adjuvant.

The source and quality of each component in this embodiment were the same as those in the embodiment 1.

Embodiment 10

In this embodiment, the immune effects of the composite vaccine adjuvants in embodiment 1, embodiment 2 and embodiment 3 were proved by animal experiments.

Test 1: Used the Composite Vaccine Adjuvant in Embodiment 1.

A. Immunization

ICR mice was divided into six groups, such as a composite vaccine adjuvant group, a single sodium ferulate adjuvant group, a single zinc hydroxide adjuvant group, an aluminum adjuvant control group, an adjuvant-free group and an blank group, 25 mice in each group. Both of the total volume of vaccines and the composite vaccine adjuvant for injection were 0.1 ml.

In the composite vaccine adjuvant group, the composite vaccine adjuvant in the embodiment 1 (sodium ferulate 10 mg and zinc hydroxide 1 mg) and hepatitis B surface antigen 5 μg were mixed and dissolved into physiological saline 0.1 ml, then were injected into mice subcutaneously.

In the single sodium ferulate adjuvant group, sodium ferulate 10 mg and hepatitis B surface antigen 5 μg were mixed and dissolved into physiological saline 0.1 ml, and then were injected into mice subcutaneously.

In the single zinc hydroxide adjuvant group, zinc hydroxide 1 mg and hepatitis B surface antigen 5 μg were mixed and dissolved into physiological saline 0.1 ml, and then were injected into mice subcutaneously.

In the aluminum adjuvant control group, aluminum hydroxide 0.4 mg and hepatitis B surface antigen 5 μg were mixed and dissolved into physiological saline 0.1 ml, and then were injected into mice subcutaneously.

In the adjuvant-free group, hepatitis B surface antigen 5 μg were mixed and dissolved into physiological saline 0.1 ml, and then were injected into mice subcutaneously.

In the blank group, each mouse was injected with physiological saline 0.1 ml.

Immunization schemes: three times immunization in total, subcutaneous injection of ICR mice in 0, 1, 6 month respectively.

B. ELISA Detection of Serum Anti-HBs IgG Level

After 4, 8, 16, 24, 32 weeks of the initial immunization, collect vein blood of mice tail, separate serum, then use ELISA to detect the serum anti-HBs IgG level by method of protein microporous kit, the specific method comprising the following steps: dissolving the 40 μL HBsAg into 10 ml 1× coating diluent, well mixing, coating 96-well ELISA plate, 100 μl/well; placing the ELISA plate in the wet box overnight at 4° C.; removing the liquid in the well and patting to clean; adding in 1×BSA, 200 μl/well, placing the ELISA plate in the wet box for 1 h at 37° C.; removing the liquid in the well and patting to clean; diluting serum by double ratio, and then adding it into the ELISA plate, 100 μl/well, placing it in the wet box for 1 h at 37° C.; then washing the plate 4 times by lotion prepared by kit, 5 mins each time, patting the ELISA plate to clean at the last time; adding in second antibody prepared by kit, 100 μl/well (sheep anti-mouse IgG binding peroxidase), placing it in the wet box for 1 h at 37° C.; washing the plate 4 times by lotion, 5 mins each time, patting the ELISA plate cleanly at the last time; adding in the chromogenic reagent prepared by kit, 100 μl/well, chromogenic reacting for 10-25 min away from light; adding in the stop solution 100 μl each well; placing the ELISA plate into enzyme-labelled instrument and reading plate at 405 nm C. Data Analysis The obtained experimental data were analyzed by single factor analysis of variance using SPSS11.5 statistics software, and $P<0.05$ having a statistically significance.

Table 1 shows the mice serum antibody levels of anti-HBs IgG of each experimental group after using the composite vaccine adjuvant provided in the Example 1 within 28 weeks (1:N).

TABLE 1

| Time/ weeks | Composite vaccine adjuvant group | Single sodium ferulate adjuvant group | Single zinc hydroxide adjuvant group | Aluminum adjuvant control group | Adjuvant-free group | Blank group |
|---|---|---|---|---|---|---|
| 4 | 135 | 46 | 110 | 8 | 19 | 0 |
| 8 | 965 | 89 | 750 | 615 | 63 | 0 |
| 12 | 1235 | 79 | 683 | 149 | 50 | 0 |
| 16 | 540 | 49 | 520 | 101 | 19 | 0 |
| 20 | 419 | 35 | 316 | 61 | 4 | 0 |
| 24 | 236 | 21 | 194 | 19 | 0 | 0 |
| 28 | 196 | 40 | 63 | 8 | 0 | 0 |

Figure 2:
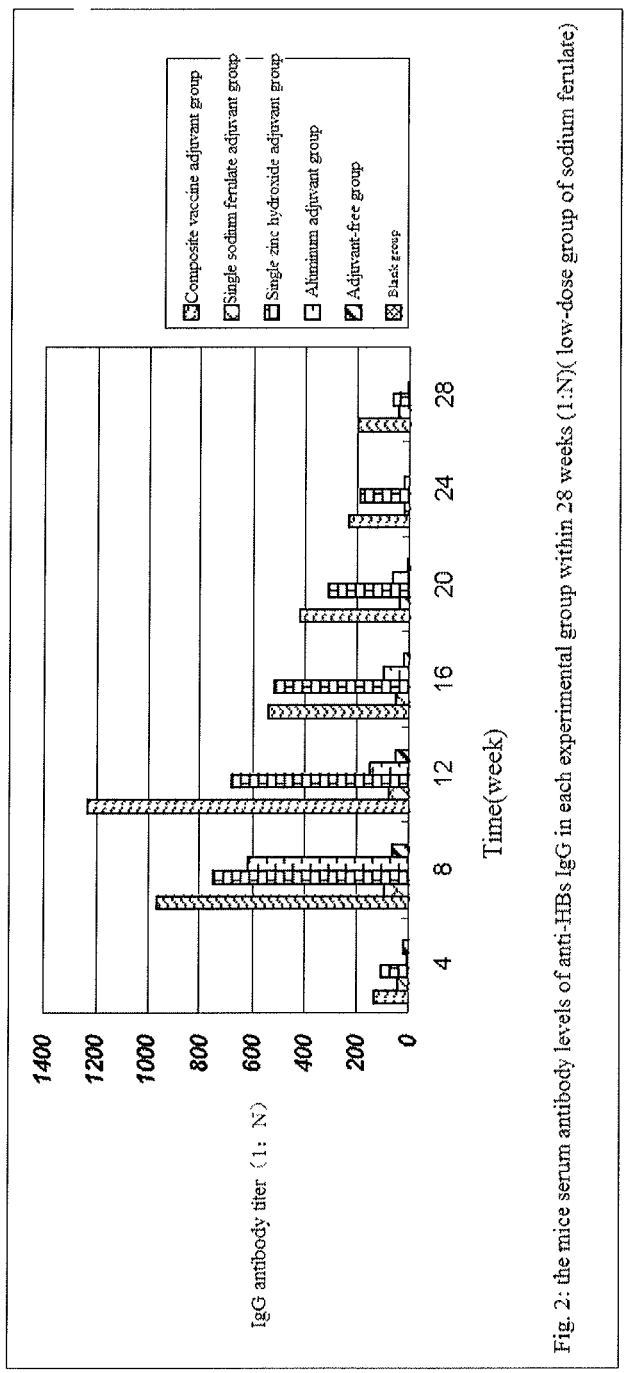
FIG. 2 shows the mice serum antibody levels of anti-HBs IgG of each experimental group after using the composite vaccine adjuvant provided in Example 1 within 28 weeks (1:N)

The data analysis showed that every experimental group can produce anti-HBsIgG antibody from the fourth week and achieve the peak at the eighth week generally. The immune effects of the composite vaccine adjuvant group was the best, and the antibody titers levels of the composite vaccine adjuvant group were higher than those of the adjuvant-free group significantly within 28 weeks, P<0.05, and maintained a high level during the detection. The antibody levels of all the experimental groups added in adjuvant were significantly higher than those of the adjuvant-free group. Among them, the antibody levels of the composite vaccine adjuvant group and the single zinc hydroxide adjuvant group were significantly higher than those of the aluminum adjuvant control group (P<0.05). The antibody levels of the composite vaccine adjuvant group were significantly higher than those of the single zinc hydroxide adjuvant group (P<0.05). It suggested that the composite vaccine adjuvant group had the function that can enhance the immune effect of the hepatitis B surface antigen, the enhancement effect of humoral immunity being superior to the single zinc hydroxide adjuvant group and the single sodium ferulate adjuvant group. The mice serum antibody levels of anti-HBs IgG in each experimental group within 28 weeks can be seen in FIG. 2 (low-dose group of sodium ferulate).

The hepatitis B surface antigen used in this test was provided by Shenzhen Kangtai Biological Products CO., Ltd. The sodium ferulate was purchased from Fujian Mindong Lijiexun Pharmaceutical Co., Ltd. The zinc hydroxide was provided by the Tianjin Guangfu Fine Chemical Research Institute.

Test 2 Used the Composite Vaccine Adjuvant in the Embodiment 2.

A. Immunization

ICR mice were divided into six groups, such as a composite vaccine adjuvant group, a single sodium ferulate adjuvant control group, a single zinc hydroxide adjuvant group, an aluminum adjuvant group, an adjuvant-free group and a blank group, 25 mice in each group. Both of the total volume of vaccine for injection and of the composite vaccine adjuvant were 0.1 ml.

In the composite vaccine adjuvant group, composite vaccine adjuvant in the embodiment 2 (sodium ferulate 25 mg and zinc hydroxide 1 mg) and hepatitis B surface antigen 5 μg were mixed and dissolved into physiological saline 0.1 ml, then were injected into mice subcutaneously.

In the single sodium ferulate adjuvant group, sodium ferulate 25 mg and hepatitis B surface antigen 5 μg were mixed and dissolved into physiological saline 0.1 ml, and then were injected into mice subcutaneously.

In the single zinc hydroxide adjuvant group, zinc hydroxide 1 mg and hepatitis B surface antigen 5 μg were mixed and dissolved into physiological saline 0.1 ml, and then were injected into mice subcutaneously.

In the aluminum adjuvant control group, aluminum hydroxide 0.4 mg and hepatitis B surface antigen 5 μg were mixed and dissolved into physiological saline 0.1 ml, and then were injected into mice subcutaneously.

In the adjuvant-free group, hepatitis B surface antigen 5 μg were dissolved into physiological saline 0.1 ml, and then were injected into mice subcutaneously.

In the blank group, each mouse was injected with physiological saline 0.1 ml.

Immunization schemes: three times immunization in total, subcutaneous injection of ICR mice in 0, 1, 6 month respectively.

B. ELISA Detection of Serum Anti-HBs IgG Level

After 4, 8, 16, 24, 32 weeks of the initial immunization, collect vein blood of mouse tail, separate serum, then use ELISA to detect the serum anti-HBs IgG level by method of protein microporous kit, the specific method comprising the following steps: dissolving the 40 μL HBsAg into 10 ml 1× coating diluent, well mixing, coating 96-well ELISA plate, 100 μl/well; placing the ELISA plate in the wet box overnight at 4° C.; removing the liquid in the well and patting to clean; adding in 1×BSA, 200 μl/well, placing the ELISA plate in the wet box for 1 h at 37° C.; removing the liquid in the well and patting to clean; diluting serum by double ratio, and then adding it into the ELISA plate, 100 μl/well, placing it in the wet box for 1 h at 37° C.; then washing the plate 4 times by lotion prepared by kit, 5 mins each time, patting the ELISA plate to clean at the last time; adding in second antibody prepared by kit, 100 μl/well (sheep anti-mouse IgG binding peroxidase), placing it in the wet box for 1 h at 37° C.; washing the plate 4 times by lotion, 5 mins each time, patting the ELISA plate cleanly at the last time; adding in the chromogenic reagent prepared by kit, 100 μl/well, chromogenic reacting for 10-25 min away from light; adding in the stop solution 100 μl each well; placing the ELISA plate into enzyme-labelled instrument and reading plate at 405 nm C. Data Analysis The obtained experimental data were analyzed by single factor analysis of variance using SPSS11.5 statistics software, and P<0.05 having a statistically significance.

Table 2 shows the mice serum antibody levels of anti-HBs IgG of each experimental group after using the composite vaccine adjuvant provided in the Example 1 within 28 weeks (1:N).

TABLE 2

| Time/ weeks | Composite vaccine adjuvant group | Single sodium ferulate adjuvant group | Single zinc hydroxide adjuvant group | Aluminum adjuvant control group | Adjuvant-free group | Blank group |
|---|---|---|---|---|---|---|
| 4 | 219 | 40 | 109 | 8 | 21 | 0 |
| 8 | 1256 | 71 | 754 | 640 | 59 | 0 |
| 12 | 1468 | 59 | 686 | 163 | 61 | 0 |
| 16 | 985 | 47 | 602 | 111 | 21 | 0 |
| 20 | 763 | 40 | 309 | 73 | 6 | 0 |
| 24 | 463 | 37 | 201 | 20 | 0 | 0 |
| 28 | 296 | 41 | 72 | 11 | 0 | 0 |

Figure 3:
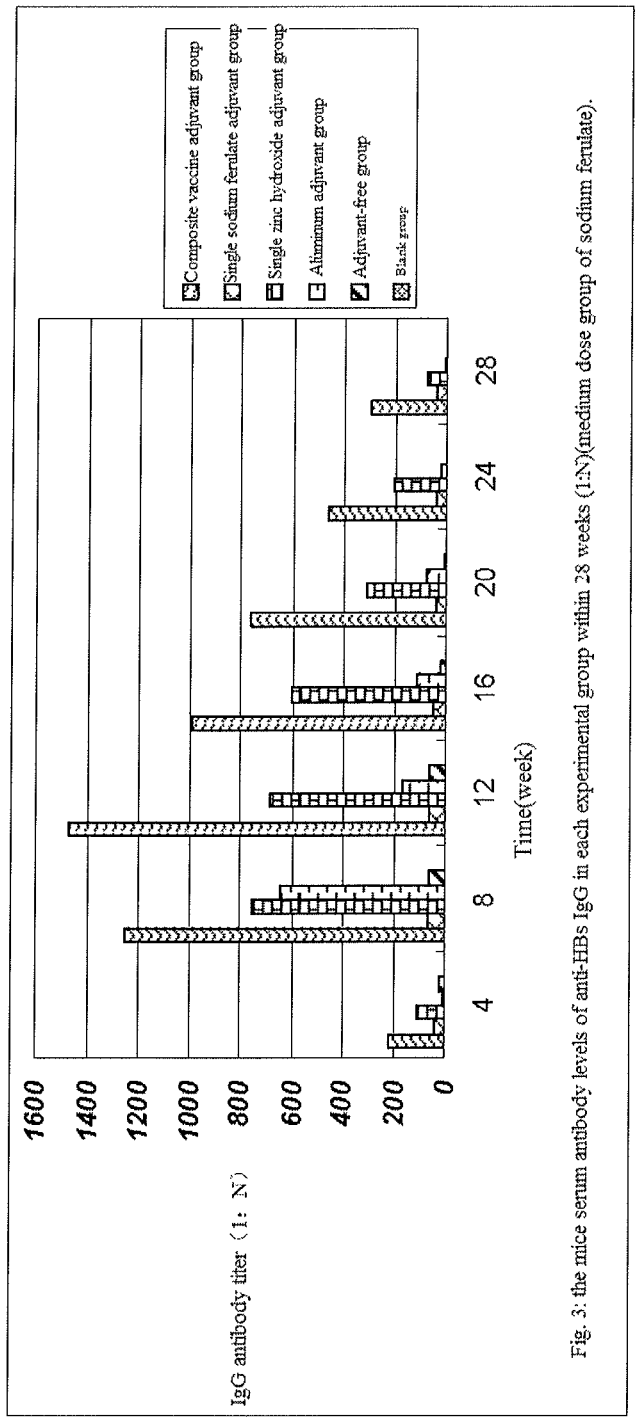
FIG. 3 shows the mice serum antibody levels of anti-HBs IgG of each experimental group after using the composite vaccine adjuvant provided in Example 2 within 28 weeks (1:N)

The data analysis showed that every experimental group can produce anti-HBsIgG antibody from the fourth week and achieve the peak at the eighth week generally. The immune effects of the composite vaccine adjuvant group was the best, the antibody titers levels of the composite vaccine adjuvant group were higher than those of the adjuvant-free group significantly within 28 weeks and maintained a high level during the detection (P<0.05). The antibody levels of all the experimental groups added in adjuvant were significantly higher than those of the adjuvant-free group. Among them, the antibody levels of the composite vaccine adjuvant group and the single zinc hydroxide adjuvant group were significantly higher than those of the aluminum adjuvant control group (P<0.05). The antibody levels of the composite vaccine adjuvant group were significantly higher than those of the single zinc hydroxide adjuvant group (P<0.05). It suggested that the composite vaccine adjuvant group had the function that can enhance the immune effect of the hepatitis B surface antigen, the enhancement effect of humoral immunity being superior to the single zinc hydroxide adjuvant group and the single sodium ferulate adjuvant group. The mice serum antibody levels of anti-HBs IgG in each experimental group within 28 weeks can be seen in FIG. 3 (medium dose group of sodium ferulate).

The hepatitis B surface antigen used in this test was provided by Shenzhen Kangtai Biological Products CO., Ltd. The sodium ferulate was purchased from Fujian Mindong Lijiexun Pharmaceutical Co., Ltd. The zinc hydroxide was provided by the Tianjin Guangfu Fine Chemical Research Institute.

Test 3 Used the Composite Vaccine Adjuvant in Embodiment 3.

A. Immunization

ICR mice were divided into six groups, such as a composite vaccine adjuvant group, a single sodium ferulate adjuvant group, a single zinc hydroxide adjuvant group, an aluminum adjuvant control group, an adjuvant-free group and a blank group, 25 mice in each group. Both of the total volume of vaccines for injection and of the composite vaccine adjuvant were 0.1 ml.

In the composite vaccine adjuvant group, the composite vaccine adjuvant in the embodiment 3 (sodium ferulate 50 mg and zinc hydroxide 1 mg) and hepatitis B surface antigen 5 µg were mixed and dissolved into physiological saline 0.1 ml, and then were injected into mice subcutaneously.

In the single sodium ferulate adjuvant group, sodium ferulate 50 mg and hepatitis B surface antigen 5 µg were mixed and dissolved into physiological saline 0.1 ml, and then were injected into mice subcutaneously.

In the single zinc hydroxide adjuvant group, zinc hydroxide 1 mg and hepatitis B surface antigen 5 µg were mixed and dissolved into physiological saline 0.1 ml, and then were injected to mice subcutaneously.

In the aluminum adjuvant group, aluminum hydroxide 0.4 mg and hepatitis B surface antigen 5 µg were mixed and dissolved into physiological saline 0.1 ml, and then were injected into mice subcutaneously.

In the adjuvant-free group, hepatitis B surface antigen 5 µg were mixed and dissolved into physiological saline 0.1 ml, and then were injected into mice subcutaneously.

In the blank group, each mouse was injected with physiological saline 0.1 ml.

Immunization schemes: three times immunization in total, subcutaneous injection of ICR mice in 0, 1, 6 month respectively.

B. ELISA Detection of Serum Anti-HBs IgG Level

After 4, 8, 16, 24, 32 weeks of the initial immunization, collect vein blood of mouse tail, separate serum, and then use ELISA to detect the serum anti-HBs IgG level by method of protein microporous kit. The specific method comprising the following steps: dissolving the 404, HBsAg into 10 ml 1× coating diluent, well mixing, coating 96-well ELISA plate, 100 µl/well; placing the ELISA plate in the wet box overnight at 4° C.; removing the liquid in the well and patting to clean; adding in 1×BSA, 200 µl/well, placing the ELISA plate in the wet box for 1 h at 37° C.; removing the liquid in the well and patting to clean; diluting serum by double ratio, and then adding it into the ELISA plate, 100 µl/well, placing it in the wet box for 1 h at 37° C.; then washing the plate 4 times by lotion prepared by kit, 5 mins each time, patting the ELISA plate to clean at the last time; adding in second antibody prepared by kit, 100 µl/well (sheep anti-mouse IgG binding peroxidase), placing it in the wet box for 1 h at 37° C.; washing the plate 4 times by lotion, 5 mins each time, patting the ELISA plate to clean at the last time; adding in the chromogenic reagent prepared by kit, 100 µl/well, chromogenic reacting for 10-25 min away from light; adding in the stop solution 100 µl each well; placing the enzyme label plate into enzyme-labelled instrument and reading plate at 405 nm.

C. Data Analysis

The obtained experimental data were analyzed by single factor analysis of variance using SPSS11.5 statistics software, and P<0.05 having a statistically significance.

Table 3 shows the mice serum antibody levels of anti-HBs IgG of each experimental group after using the composite vaccine adjuvant provided in the Example 1 within 28 weeks (1:N).

TABLE 3

| Time/weeks | Composite vaccine adjuvant group | Single sodium ferulate adjuvant group | Single zinc hydroxide adjuvant group | Aluminum adjuvant control group | Adjuvant-free group | Blank group |
|---|---|---|---|---|---|---|
| 4 | 144 | 56 | 111 | 9 | 23 | 0 |
| 8 | 810 | 77 | 679 | 609 | 65 | 0 |
| 12 | 960 | 121 | 781 | 161 | 33 | 0 |
| 16 | 507 | 71 | 531 | 112 | 22 | 0 |
| 20 | 444 | 56 | 321 | 73 | 6 | 0 |
| 24 | 302 | 31 | 201 | 21 | 0 | 0 |
| 28 | 20 | 27 | 65 | 10 | 0 | 0 |

Figure 4:
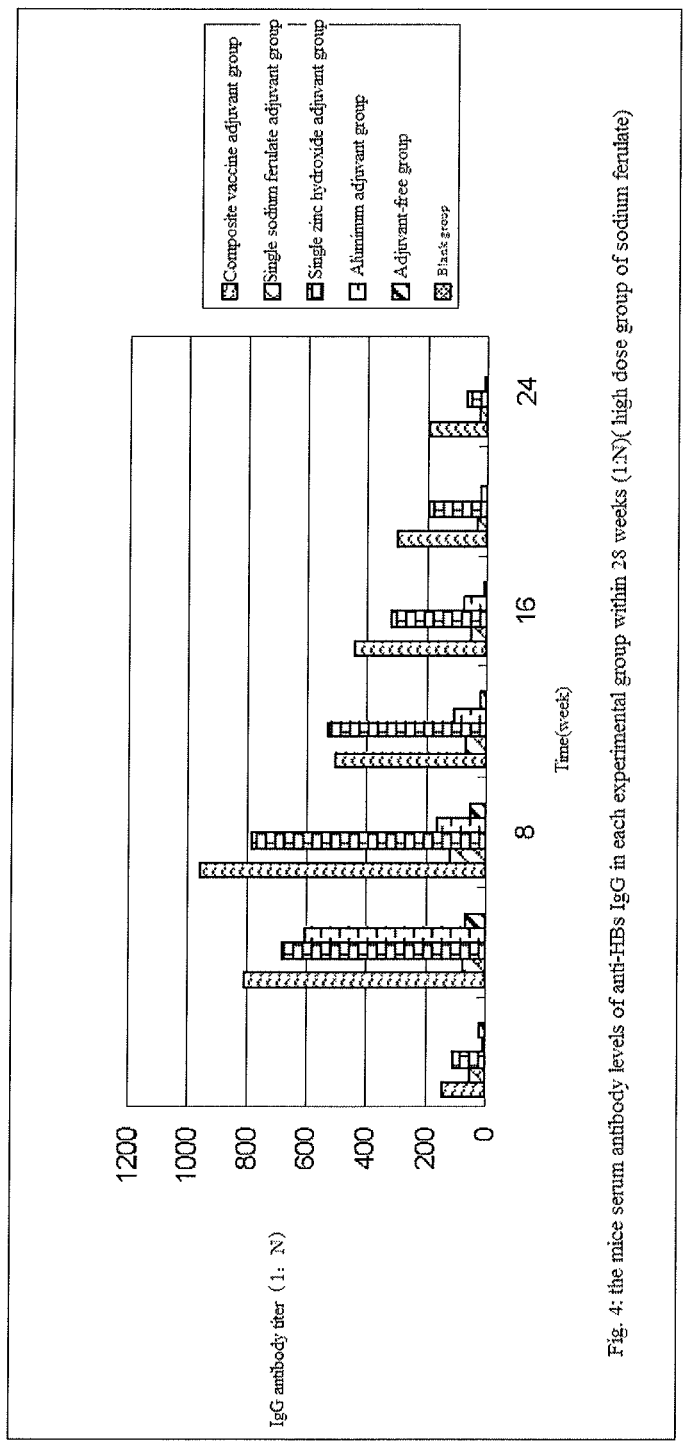
FIG. 4 shows the mice serum antibody levels of anti-HBs IgG of each experimental group after using the composite vaccine adjuvant provided in Example 3 within 28 weeks (1:N).

The data analysis showed that every experimental group can produce anti-HBsIgG antibody from the fourth week and achieve the peak at the eighth week generally. The immune effects of the composite vaccine adjuvant group was the best, the antibody titers levels of the composite vaccine adjuvant group were higher than those of adjuvant-free group significantly within 28 weeks and maintained a high level during the detection (P<0.05). The antibody levels of all the experimental groups added in adjuvant were significantly higher than those of the adjuvant-free group. Among them, the antibody levels of the composite vaccine adjuvant group and the single zinc hydroxide adjuvant group are significantly higher than those of the aluminum adjuvant control group (P<0.05). The antibody levels of the composite vaccine adjuvant group are significantly higher than those of the single zinc hydroxide adjuvant group (P<0.05). It suggested that the composite vaccine adjuvant group had the function that can enhance the immune effect of the hepatitis B surface antigen, the enhancement effect of humoral immunity being superior to the single zinc hydroxide adjuvant group and the single sodium ferulate adjuvant group. The mice serum antibody levels of anti-HBs IgG in each experimental group within 28 weeks can be seen in FIG. 4 (high dose group of sodium ferulate).

The hepatitis B surface antigen used in this test was provided by Shenzhen Kangtai Biological Products CO., Ltd. The sodium ferulate was purchased from Fujian Mindong Lijiexun Pharmaceutical Co., Ltd. The zinc hydroxide was provided by the Tianjin Guangfu Fine Chemical Research Institute.

What is claimed is:

1. A composite vaccine adjuvant consisting of sodium ferulate and zinc hydroxide in a mass ratio of 10:1~50:1.

2. The composite vaccine adjuvant according to claim 1, characterized in that said composite vaccine adjuvant consists of sodium ferulate and zinc hydroxide in a mass ratio of 10:1.

3. The composite vaccine adjuvant according to claim 1, characterized in that said composite vaccine adjuvant consists of sodium ferulate and zinc hydroxide in a mass ratio of 25:1.

4. The composite vaccine adjuvant according to claim 1, characterized in that said composite vaccine adjuvant consists of sodium ferulate and zinc hydroxide in a mass ratio of 50:1.

5. The composite vaccine adjuvant according to claim 1, characterized in that said composite vaccine adjuvant consists of sodium ferulate and zinc hydroxide in a mass ratio of 15:1.

6. The composite vaccine adjuvant according to claim 1, characterized in that said composite vaccine adjuvant consists of sodium ferulate and zinc hydroxide in a mass ratio of 20:1.

7. The composite vaccine adjuvant according to claim 1, characterized in that said composite vaccine adjuvant consists of sodium ferulate and zinc hydroxide in a mass ratio of 30:1.

8. The composite vaccine adjuvant according to claim 1, characterized in that said composite vaccine adjuvant consists of sodium ferulate and zinc hydroxide in a mass ratio of 40:1.

9. The composite vaccine adjuvant according to claim 1, characterized in that said composite vaccine adjuvant consists of sodium ferulate and zinc hydroxide in a mass ratio of 45:1.

10. A method for preparing a composite vaccine adjuvant, characterized in that said composite vaccine adjuvant consists of sodium ferulate and zinc hydroxide in a mass ratio of 10:1~50:1, and the preparation method comprises: mixing the sodium ferulate and zinc hydroxide thoroughly in the mass radio to obtain said composite vaccine adjuvant.

* * * * *